(12) United States Patent
Hsieh

(10) Patent No.: US 6,480,560 B2
(45) Date of Patent: Nov. 12, 2002

(54) METHODS AND APPARATUS FOR MOTION GATING USING CT PROJECTION DATA

(75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 35 days.

(21) Appl. No.: 09/810,926

(22) Filed: Mar. 16, 2001

(65) Prior Publication Data

US 2002/0131545 A1 Sep. 19, 2002

(51) Int. Cl.$^7$ ................................................. A61B 6/03
(52) U.S. Cl. .............................................. 378/8; 378/901
(58) Field of Search ........................... 378/4, 8, 15, 901

(56) References Cited

U.S. PATENT DOCUMENTS

| 5,165,100 A | 11/1992 | Hsieh et al. |
| 5,225,980 A | 7/1993 | Hsieh et al. |
| 5,416,815 A | 5/1995 | Hsieh |
| 5,812,628 A | 9/1998 | Hsieh |
| 5,987,091 A | * 11/1999 | Miyazaki et al. .............. 378/15 |
| 6,035,012 A | 3/2000 | Hsieh |
| 6,061,419 A | 5/2000 | Hsieh et al. |
| 6,115,487 A | 9/2000 | Toth et al. |
| 6,144,759 A | * 11/2000 | Weese et al. ................ 382/132 |
| 6,192,265 B1 | * 2/2001 | Carlsen et al. .............. 324/309 |
| 6,215,841 B1 | 4/2001 | Hsieh |
| 6,233,308 B1 | 5/2001 | Hsieh |

* cited by examiner

Primary Examiner—David V. Bruce
(74) Attorney, Agent, or Firm—Carl B. Horton, Esq.; Armstrong Teasdale LLP

(57) ABSTRACT

Methods and apparatus for reducing motion-induced artifacts in CT imaging is described. The imaging system scans a patient's heart to obtain a plurality of projection views, a differential projection is determined from the projection views, a weighting function is applied to the differential projection to minimize motion artifacts, and an inconsistency index is determined from the differential projection, and the inconsistency index is used to locate an image reconstruction location. This method directly measures the mechanics of the heart, rather than an electrical signal and utilizes projection data to select the best locations to minimize image artifact.

37 Claims, 2 Drawing Sheets

METHODS AND APPARATUS FOR MOTION GATING USING CT PROJECTION DATA

BACKGROUND OF THE INVENTION

This invention relates generally to methods and apparatus for CT imaging and other radiation imaging systems and, more particularly, to utilizing a method to minimize motion artifacts caused by cardiac motion.

In at least some "computed tomography" (CT) imaging system configurations, an x-ray source projects a fan-shaped beam which is collimated to lie within an X-Y plane of a Cartesian coordinate system, generally referred to as an "imaging plane". The x-ray beam passes through an object being imaged, such as a patient. The beam, after being attenuated by the object, impinges upon an array of radiation detectors. The intensity of the attenuated beam radiation received at a detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged, so the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodetectors adjacent to the scintillator. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units," which are used to control the brightness of a corresponding pixel on a cathode ray tube display.

To reduce the total scan time required for multiple slices, a "helical" scan may be performed. To perform a "helical" scan, the patient is moved in the z-axis synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed.

Known cardiac CT scanners utilize "electro-cardio-gram" (EKG) signals when acquiring scan data. Typically, a plurality of leads are connected to a patient to measure the EKG signal, which indirectly represents a cardiac cycle. The cardiac cycle includes a period of relaxation and dilation of the heart cavities known as diastole, and a period of contraction of the heart during which blood is ejected from the ventricles known as systole. A typical period of time for one cardiac cycle is slightly less than one second. Thus, a heart goes through a substantial portion of its cycle during one gantry revolution. Motion induced image artifacts result from heart motion.

To suppress the image artifact, some cardiac CT scanners correlate the EKG electrical signals with a plurality of mechanical signals of the heart. The electrical signals and the mechanical signals, however, cannot be precisely correlated for each patient. Therefore, extra views of projection data are acquired based on EKG signals. A radiologist then visually selects a best image from the set of reconstructed images.

BRIEF SUMMARY OF THE INVENTION

Methods and apparatus for reducing motion-induced artifacts in computed tomography (CT) imaging are described. In one aspect, a method for imaging a heart is provided in which the heart is scanned to obtain projection data for a plurality of projection views. A differential projection is determined based on a first and a last projection view. A weighting function is applied to the differential projection to minimize motion artifacts, and an inconsistency index is generated from the differential projection, which is used to identify an image reconstruction location.

In another aspect, a processor in the imaging system is programmed to acquire projection data for a plurality of projection views of the heart. The processor is programmed to determine a differential projection based on a first and a last projection set, apply a weighting function to the differential projection and generate an inconsistency index to determine an image reconstruction location.

In yet another aspect, a computer-readable medium in the imaging system is provided which comprises a plurality of records of projection data. A program residing on the computer-readable medium utilizes a plurality of rules to generate a differential projection based on a first and a last projection view, define a weighting function that is applied to the differential projection to minimize motion induced artifacts, and utilize a plurality of rules to determine an inconsistency index to identify an image reconstruction location.

This method directly measures the mechanics of the heart, rather than an EKG electrical signal. In addition, this method utilizes projection data to select a reconstruction location to minimize motion-induced image artifact. Further, implementing the method does not require that additional hardware be used or replaced.

DETAILED DESCRIPTION OF THE INVENTION

Figure 1:
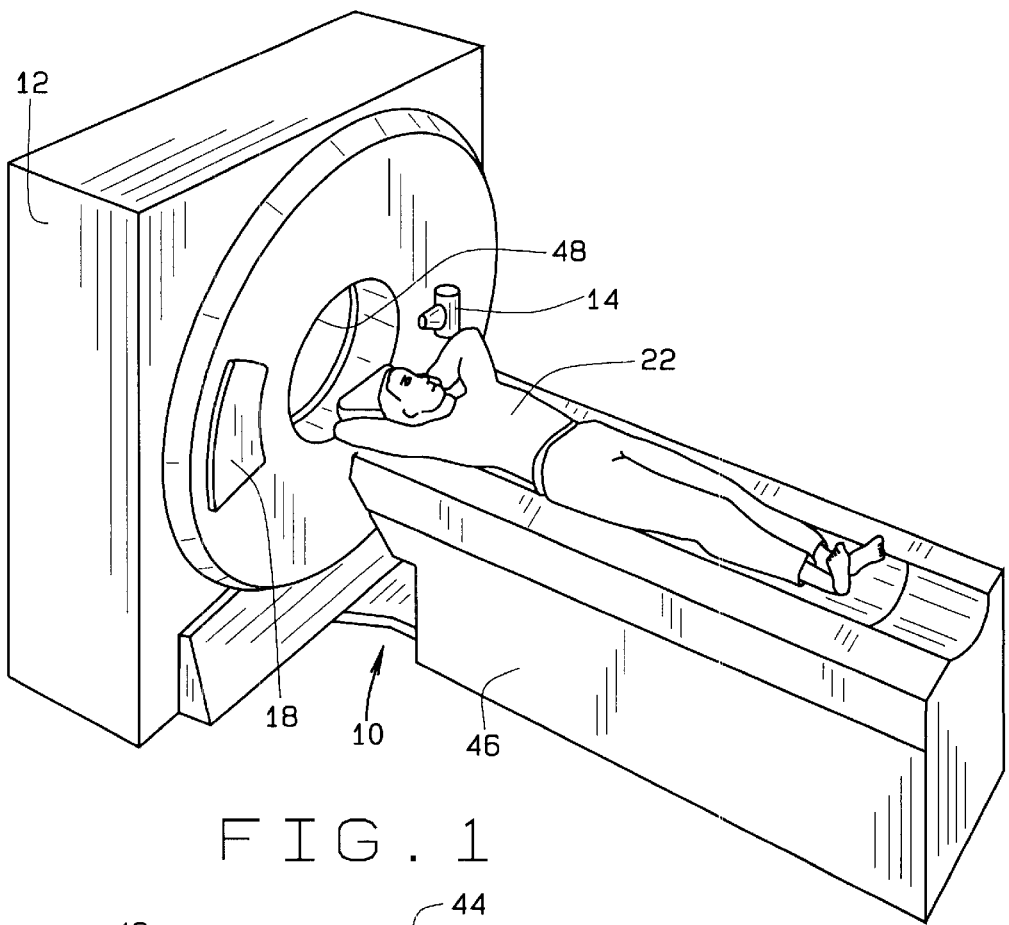
FIG. 1 is a pictorial view of a CT imaging system.
Figure 2:
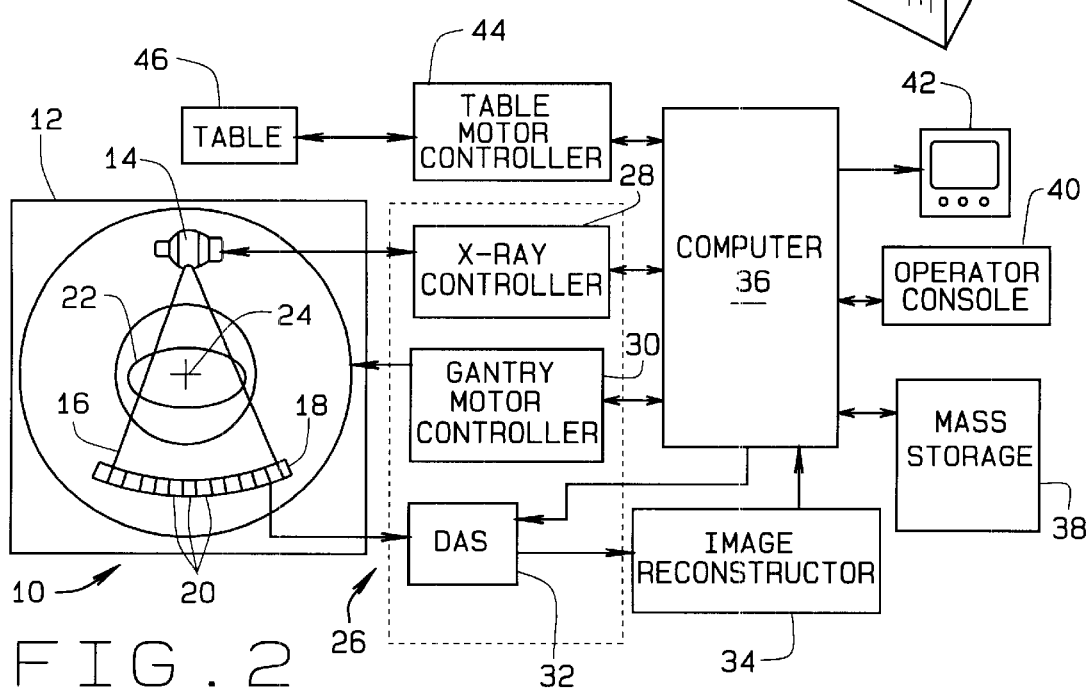
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. In one embodiment, and as shown in FIG. 2, detector elements 20 are arranged in one row so that projection data corresponding to a single image slice is acquired during a scan. In another embodiment, detector elements 20 are arranged in a plurality of parallel rows, so that projection data corresponding to a plurality of parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
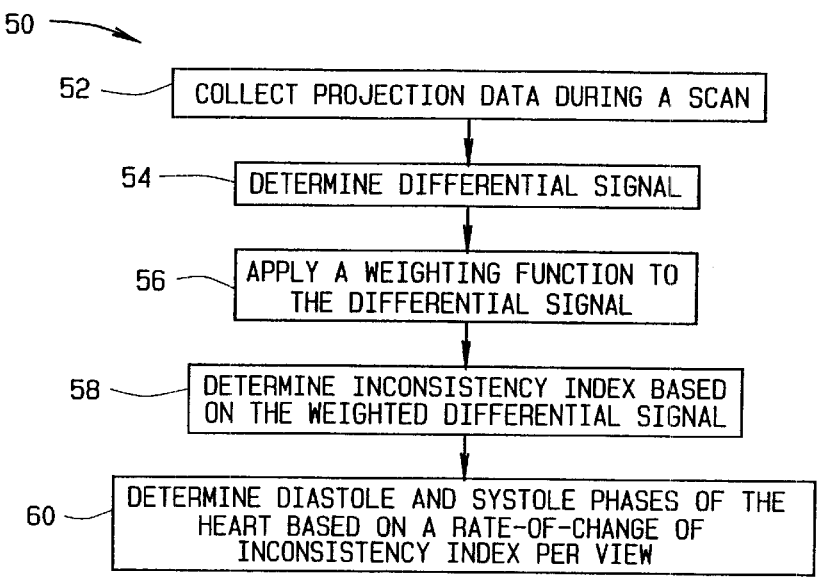
FIG. 3 is a flow chart illustrating a sequence of steps executed by the CT system to determine diastole and systole phases of a human heart.

FIG. 3 is a flow chart 50 illustrating the steps executed to determine a reconstruction location where a motion induced artifact is minimum. The method illustrated in FIG. 3 can be practiced by DAS 32 (shown in FIG. 2), image reconstructor 34 (shown in FIG. 2), or computer 36 (shown in FIG. 2). Generally, a processor in at least one of DAS 32, reconstructor 34, and computer 36 is programmed to execute the process steps described below. Of course, the method is not limited to practice in CT system 10 and can be utilized in connection with many other types and variations of imaging systems.

For a CT data set, artifacts caused by the motion of an object are introduced by the largest inconsistency present in adjacent projection views. For example, in a full scan, the discrepancy between the start and end of the scan typically represents a worst-case condition. When scanning an object with a cyclic motion, not necessarily periodic, the motion artifact is minimum when the object is roughly in the same motion state at the start and end of the scan. It is known that when the period of the motion matches exactly the cycle of the gantry speed for a half-scan and a full scan, the motion artifact is minimal.

To minimize motion artifacts, a starting projection view is determined after collecting a plurality of projection views 52. The differences between the first and the last views used in the reconstruction are determined and the starting view selected is the one which minimizes the difference. For example, to find the starting angle for a halfscan to minimize motion induced artifacts, a differential projection 54 is determined by the following relationship:

$$d(\gamma,\beta)=|P(\gamma,\beta+\gamma_m-\gamma)-P(-\gamma,\beta+\pi+\gamma_m+\gamma)|, \quad (1)$$

where $\beta$ is the projection angle, $\gamma$ is the detector angle, and $\gamma$ is the maximum detector angle. For a full scan, a differential projection 54 is determined by the following relationship:

$$d(\gamma,\beta)=|P(\gamma,\beta)-P(\gamma,\beta+2\pi)|, \quad (2)$$

where $\beta$ is the projection angle and $\gamma$ is the detector angle.

To minimize the influence of other motion induced differences, e.g., such as respiratory motion, the differential projection is multiplied by a weighting function 56. An inconsistency index 58, $\xi(\beta)$, is determined according to the following relationship:

$$\xi(\beta) = \int_{-\gamma m}^{\gamma m} w(\gamma)\,d(\gamma,\beta)\,d\gamma, \quad (3)$$

where $d(\gamma,\beta)$ is a differential projection, $\omega(\gamma)$ is a weighting function, $\gamma_m$ is a maximum detector angle, and $-\gamma_m$ is a minimum detector angle. The diastole and systole phases of the heart are determined 60 based on a rate of change of inconsistency index 58 per view.

Figure 4:
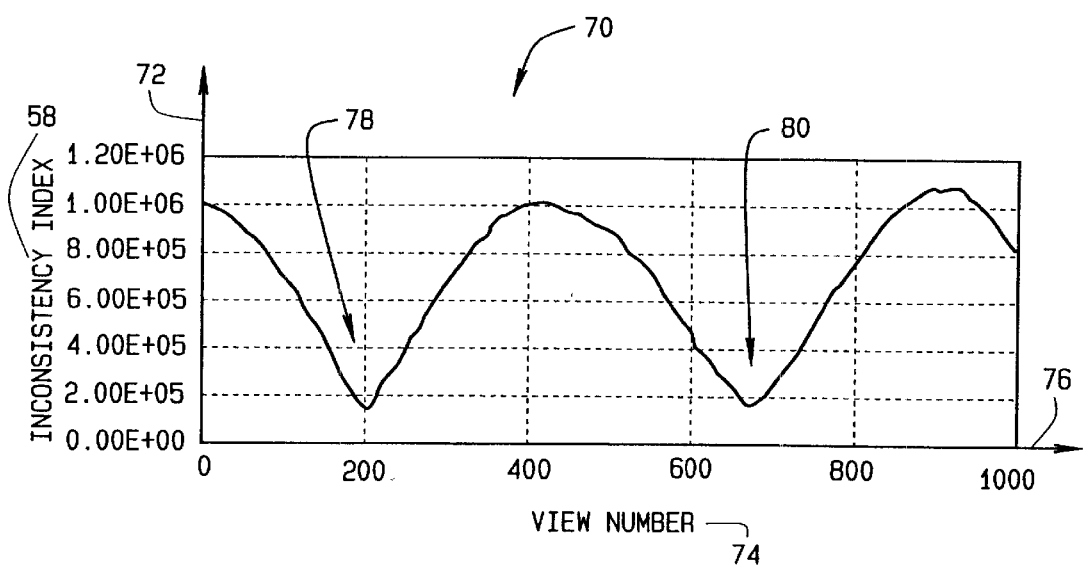
FIG. 4 is a chart illustrating view number versus inconsistency index used to determine diastole and systole phases of the heart.

Referring specifically to FIG. 4, which illustrates a chart 70 of balloon phantom (not shown). The balloon phantom is inflated and deflated at a rate of sixty-five "beats per minute" (bpm), and projection data is acquired at 0.8s by CT scanner 10 in cine mode. Inconsistency index 58, $\xi(\beta)$ is determined and plotted on an ordinate 72 and view numbers 74 are plotted on an abscissa 76. In an exemplary embodiment, a first valley 78 of a first curve occurs at view number two-hundred and a second valley 80 occurs at view number six-hundred-and-seventy. Of course, other charts of inconsistency index versus view numbers are possible with the first valley and the second valley positioned at various other view numbers. First valley 78 corresponds to the halfscan acquisition centered at the end of deflating the balloon, e.g., analagous to the end of systole in a cardiac cycle. Second valley 80 corresponds to the halfscan acquisition centered at the end of inflating the balloon, e.g., analagous to the end of diastole in a cardiac cycle. The rate-of-change, e.g., slope, of the inconsistency index near the two valleys is different. For first valley 78, e.g., the deflation case, the slope is five-thousand-eight-hundred-and-thirty-three, and for second valley 80, e.g., the inflation case, the slope is three-thousand-six-hundred-and-forty. Therefore, by comparing the inconsistency index slope, the systole and diastole phases 62 of the heart are determined, where steeper slope values correspond to the systolic phase. The acquisition center at the end of diastole phase of the heart should provide minimum motion artifact.

In another embodiment, a plurality of images are reconstructed based on views from the end of systole phase of the heart to the end of the diastole phase of the heart. These reconstructed images represent different phases of the heart and depict the cardiac cycle when viewed in sequence.

In yet another embodiment, a CT system 10 includes a computer program residing on a computer-readable medium within mass storage 38 for reconstructing the image. A plurality of records of projection data for a plurality of projection views are stored on the computer-readable medium. A plurality of records of differential projections are generated from the records of projection data. A plurality of rules apply a weighting function to the records of differential projections, and a plurality of rules determine records of inconsistency index for each record of projection view.

This method of imaging the heart is based on direct measurements of the mechanics of the heart, rather than an EKG electrical signal. In addition, this method utilizes projection data to select a reconstruction location to minimize motion induced image artifact. Further, implementing the method does not require that additional hardware be used or replaced.

While the invention has been described in terms of various specific embodiments, those skilled in the art will recognize that the invention can be practiced with modification within the spirit and scope of the claims.

What is claimed is:

1. A method for determining a reconstruction location when imaging a heart with a computed tomographic imaging system, said method comprising the steps of:
    scanning a patient to acquire projection data for a plurality of projection views;
    determining a differential projection from the projection data;
    applying a weighting function to the differential projection; and
    determining an inconsistency index to identify a reconstruction location.

2. A method in accordance with claim 1 wherein said step of determining a differential projection comprises the step of determining a differential projection for a half scan according to the relationship:

$$d(\gamma,\beta)=|P(\gamma,\beta+\gamma_m-\gamma)-P(-\gamma,\beta+\pi+\gamma_m+\gamma)|,$$

where $\beta$ is a projection angle, $\gamma$ is a detector angle, and $\gamma_m$ is a maximum detector angle.

3. A method in accordance with claim 1 wherein said step of determining a differential projection comprises the step of determining a differential projection for a full scan according to the relationship:

$$d(\gamma,\beta)=|P(\gamma,\beta)-P(\gamma,\beta+2\pi)|,$$

where $\beta$ is a projection angle and $\gamma$ is a detector angle.

4. A method in accordance with claim 1 wherein said step of applying a weighting function comprises the step of multiplying a plurality of differential projections based on a plurality of detector angles, $\gamma$, by the weighting function, $\omega(\gamma)$.

5. A method in accordance with claim 4 wherein the inconsistency index comprises the relationship:

$$\xi(\beta) = \int_{-\gamma m}^{\gamma m} w(\gamma)\,d(\gamma, \beta)d\gamma,$$

where $d(\gamma,\beta)$ is a differential projection, $\omega(\gamma)$ is a weighting function, $\gamma_m$ is a maximum detector angle, and $-\gamma_m$ is a minimum detector angle.

6. A method in accordance with claim 5 wherein said step of determining an inconsistency index comprises the step of determining at least one inconsistency index slope.

7. A method in accordance with claim 6 wherein said step of determining at least one inconsistency index slope further comprises the step of determining at least a systolic phase and a diastole phase.

8. A method in accordance with claim 7 wherein said step of determining the diastole phase comprises the step of determining a reconstruction location that is located at the end of the diastole phase.

9. An imaging system comprising a computer, a gantry having a detector array, an x-ray source for radiating an x-ray beam along an imaging plane toward a detector array including a plurality of detector cells, the computer coupled to the x-ray source and the gantry, said imaging system configured to:
    acquire projection data for a plurality of projection views;
    determine a differential projection based on a first and last projection view;
    apply a weighting function to said differential projection; and
    determine an inconsistency index to identify a reconstruction location.

10. An imaging system in accordance with claim 9 wherein said differential projection comprises a differential projection for at least a half scan and a full scan.

11. An imaging system in accordance with claim 10 wherein said differential projection for a half-scan comprises the relationship:

$$d(\gamma,\beta)=|P(\gamma,\beta+\gamma_m-\gamma)-P(-\gamma,\beta+\pi+\gamma_m+\gamma)|,$$

where $\beta$ is a projection angle, $\gamma$ is a detector angle, and $\gamma_m$ is a maximum detector angle.

12. An imaging system in accordance with claim 10 wherein said differential projection for a full scan comprises the relationship:

$$d(\gamma,\beta)=|P(\gamma,\beta)-P(\gamma,\beta+2\pi)|,$$

where $\beta$ is a projection angle and $\gamma$ is a detector angle.

13. An imaging system in accordance with claim 9 wherein said imaging system configured to multiply a plurality of differential projections, $d(\gamma,\beta)$, based on a plurality of detector angles, $\gamma$, by said weighting function, $\omega(\gamma)$.

14. An imaging system in accordance with claim 13 wherein said inconsistency index comprises the relationship:

$$\xi(\beta) = \int_{-\gamma m}^{\gamma m} w(\gamma)\,d(\gamma, \beta)d\gamma,$$

where $d(\gamma,\beta)$ is a differential projection, $\omega(\gamma)$ is a weighting function, $\gamma_m$ is a maximum detector angle, and $-\gamma_m$ is a minimum detector angle.

15. An imaging system in accordance with claim 14 wherein said imaging system configured to determine at least one inconsistency index slope.

16. An imaging system in accordance with claim 15 wherein said imaging system configured to determine at least a systolic phase and a diastole phase based on at least one inconsistency index slope.

17. An imaging system in accordance with claim 16 wherein said imaging system configured to determine a reconstruction location that is located at the end of the diastole phase.

18. A processor programmed to determine a reconstruction location in an imaging system, said processor configured to:
    acquire projection data for a plurality of projection views;
    determine a differential projection based on a first and last projection view;
    apply a weighting function to said differential projection;
    determine an inconsistency index;
    determine at least one inconsistency index slope to determine at least a systolic phase and diastole phase; and
    identify a reconstruction location based on a location of the end of the diastole phase.

19. A processor in accordance with claim 18 wherein said processor configured to determine said differential projection comprising at least one of a half scan and a full scan.

20. A processor in accordance with claim 19 wherein said processor configured to determine said half scan differential projection according to the relationship:

$$d(\gamma,\beta)=|P(\gamma,\beta+\gamma_m-\gamma)-P(-\gamma,\beta+\pi+\gamma_m+\gamma)|,$$

where $\beta$ is a projection angle, $\gamma$ is a detector angle, and $\gamma_m$ is a maximum detector angle.

21. A processor in accordance with claim 19 wherein said processor configured to determine said full scan differential projection according to the relationship:

$$d(\gamma,\beta)=|P(\gamma,\beta)-P(\gamma,\beta+2\pi)|,$$

where $\beta$ is a projection angle and $\gamma$ is a detector angle.

22. A processor in accordance with claim 18 wherein said processor configured to multiply a plurality of differential projections, $d(\gamma,\beta)$, based on a plurality of detector angles, $\gamma$, by said weighting fuinction, $\omega(\gamma)$.

23. A processor in accordance with claim 22 wherein said processor configured to determine said inconsistency index according to the relationship:

$$\xi(\beta) = \int_{-\gamma m}^{\gamma m} w(\gamma)d(\gamma,\beta)d\gamma,$$

where $d(\gamma,\beta)$ is a differential projection, $\omega(\gamma)$ is a weighting function, $\gamma_m$ is a maximum detector angle, and $-\gamma_m$ is a minimum detector angle.

24. A computer-readable medium in an imaging system, said computer-readable medium comprising:
- records of projection data for a plurality of projection views;
- records of differential projections based on said records of projection data;
- a plurality of rules to apply a weighting function to said records of differential projection;
- a plurality of rules to determine records of inconsistency index for each projection view; and
- a plurality of rules to identify a reconstruction location based on said records of inconsistency index.

25. A computer-readable medium according to claim 24 wherein said differential projection comprises a differential projection for at least a half scan and a full scan.

26. A computer-readable medium according to claim 25 wherein said half scan differential projection comprises the relationship:

$$d(\gamma,\beta)=|P(\gamma,\beta+\gamma_m-\gamma)-P(-\gamma,\beta+\pi+\gamma_m+\gamma)|,$$

where $\beta$ is a projection angle, $\gamma$ is a detector angle, and $\gamma_m$ is a maximum detector angle.

27. A computer-readable medium according to claim 25 wherein said full scan differential projection comprises the relationship:

$$d(\gamma,\beta)=|P(\gamma,\beta)-P(\gamma,\beta+2\pi)|,$$

where $\beta$ is a projection angle and $\gamma$ is a detector angle.

28. A computer-readable medium according to claim 24 wherein said weighting function comprises a plurality of differential projections, $d(\gamma,\beta)$, based on a plurality of detector angles, $\gamma$, multiplied by said weighting function, $\omega(\gamma)$.

29. A computer-readable medium according to claim 28 wherein said inconsistency index comprises the relationship:

$$\xi(\beta) = \int_{-\gamma m}^{\gamma m} w(\gamma)d(\gamma,\beta)d\gamma,$$

where $d(\gamma,\beta)$ is a differential projection, $\omega(\gamma)$ is a weighting function, $\gamma_m$ is a maximum detector angle, and $-\gamma_m$ is a minimum detector angle.

30. A computer-readable medium according to claim 24 wherein said reconstruction location is identified as at least one of an end of a diastole phase of the heart and an end of a systole phase of the heart.

31. A computer-readable medium according to claim 30 wherein said computer-readable medium further comprises a plurality of records of reconstruction images.

32. A computer-readable medium according to claim 31 wherein said computer-readable medium further comprises a plurality of records of reconstruction images that depict at least one cardiac cycle.

33. An computer tomographic imaging system comprising a computer, a gantry having a detector array, an x-ray source for radiating an x-ray beam along an imaging plane toward a detector array including a plurality of detector cells, the computer coupled to the x-ray source and the gantry, said imaging system configured to:
- acquire projection data for a plurality of projection views;
- determine a differential projection based on a first and last projection view;
- apply a weighting function to said differential projection;
- generate at least one inconsistency index slope based on an inconsistency index to determine at least a systolic phase and a diastole phase; and
- determine a reconstruction location that is located at the end of the diastole phase.

34. An imaging system in accordance with claim 33 wherein said differential projection comprises a differential projection for at least a half scan and a full scan.

35. An imaging system in accordance with claim 34 wherein said half scan differential projection comprises the relationship:

$$d(\gamma,\beta)=|P(\gamma,\beta+\gamma_m-\gamma)-P(-\gamma,\beta+\pi+\gamma_m+\gamma)|,$$

where $\beta$ is a projection angle, $\gamma$ is a detector angle, and $\gamma_m$ is a maximum detector angle.

36. An imaging system in accordance with claim 34 wherein said full scan differential projection comprises the relationship:

$$d(\gamma,\beta)=|P(\gamma,\beta)-P(\gamma,\beta+2\pi)|,$$

where $\beta$ is a projection angle and $\gamma$ is a detector angle.

37. An imaging system in accordance with claim 33 wherein said inconsistency index comprises the relationship:

$$\xi(\beta) = \int_{-\gamma m}^{\gamma m} w(\gamma)d(\gamma,\beta)d\gamma,$$

where $d(\gamma,\beta)$ is a differential projection, $\omega(\gamma)$ is a weighting function, $\gamma_m$ is a maximum detector angle, and $-\gamma_m$ is a minimum detector angle.

* * * * *